United States Patent
Vandine

(10) Patent No.: US 8,851,073 B2
(45) Date of Patent: Oct. 7, 2014

(54) PATIENT INTERFACE HAVING AN INTEGRATED SYSTEM FOR COMMUNICATING DATA TO A VENTILATOR

(75) Inventor: Joseph Douglas Vandine, Newark, CA (US)

(73) Assignee: Covidien LP, Mansfield, MA (US)

( * ) Notice: Subject to any disclaimer, the term of this patent is extended or adjusted under 35 U.S.C. 154(b) by 1889 days.

(21) Appl. No.: 11/537,380

(22) Filed: Sep. 29, 2006

(65) Prior Publication Data

US 2008/0078388 A1    Apr. 3, 2008

(51) Int. Cl.
| | | |
|---|---|---|
| *A61B 5/08* | (2006.01) | |
| *A61B 5/04* | (2006.01) | |
| *A62B 7/00* | (2006.01) | |
| *A62B 18/02* | (2006.01) | |
| *A61M 16/00* | (2006.01) | |
| *A62B 18/08* | (2006.01) | |
| *A61N 1/362* | (2006.01) | |
| *A61M 16/04* | (2006.01) | |
| *A61M 16/08* | (2006.01) | |
| *A61M 16/06* | (2006.01) | |

(52) U.S. Cl.
CPC ............ *A61M 16/04* (2013.01); *A61M 16/0816* (2013.01); *A61M 16/0875* (2013.01); *A61M 16/0833* (2013.01); *A61M 2205/3569* (2013.01); *A61M 16/06* (2013.01); *A61M 2205/35* (2013.01)
USPC ............ 128/204.21; 128/205.23; 128/206.21; 128/205.25; 128/206.11; 128/206.12; 128/206.18; 128/206.24; 128/206.26; 128/206.27; 128/206.28; 128/207.11; 128/207.13; 128/207.18; 600/18; 600/534; 600/538; 600/544; 600/545; 600/537

(58) Field of Classification Search
CPC ..................................................... A61B 5/1135
USPC ............ 128/205.23, 206.21, 205.25, 206.11, 128/206.18, 206.24, 206.26, 206.27, 128/206.28, 207.11, 207.13, 207.18; 600/534, 537, 538, 544, 545
See application file for complete search history.

(56) References Cited

U.S. PATENT DOCUMENTS

| | | | |
|---|---|---|---|
| 4,924,862 A | 5/1990 | Levinson | 128/207.16 |
| 5,218,970 A | 6/1993 | Turnbull et al. | 128/748 |

(Continued)

FOREIGN PATENT DOCUMENTS

| | | | | |
|---|---|---|---|---|
| DE | 100 21 783 A1 | 11/2000 | | A61M 16/00 |
| EP | 1 127 583 A2 | 8/2001 | | A61M 16/08 |

(Continued)

OTHER PUBLICATIONS

International Search Report and Written Opinion PCT/US2007/079687, 13 pages, Jan. 29, 2008.

(Continued)

*Primary Examiner* — Patricia Bianco
*Assistant Examiner* — Tarla Patel
(74) *Attorney, Agent, or Firm* — Fletcher Yoder, P.C.

(57) ABSTRACT

A medical device may include a patient interface for use in a breathing assistance system, an electronic device coupled to the patient interface, and one or more electrical conductors at least partially integrated with the patient interface. The patient interface may include a connection end configured for receiving gas communicated by a gas delivery apparatus, and a patient end configured for insertion into or more breathing passageways of a patient. The one or more electrical conductors at least partially integrated with the patient interface may be capable of facilitating communication of electrical signals between the electronic device and the gas delivery apparatus when the patient interface is communicatively coupled to the gas delivery apparatus.

21 Claims, 6 Drawing Sheets

(56) References Cited

U.S. PATENT DOCUMENTS

| | | | |
|---|---|---|---|
| 5,235,973 A | 8/1993 | Levinson | 128/207.15 |
| 5,295,489 A | 3/1994 | Bell et al. | 128/715 |
| 5,408,546 A | 4/1995 | Slaker et al. | 385/12 |
| 5,487,383 A | 1/1996 | Levinson | 128/207.15 |
| 5,546,935 A | 8/1996 | Champeau | 128/205.23 |
| 6,411,843 B1 * | 6/2002 | Zarychta | 600/546 |
| 7,575,005 B2 * | 8/2009 | Mumford et al. | 128/205.23 |
| 7,770,579 B2 * | 8/2010 | O'Connor et al. | 128/204.21 |
| 2003/0183294 A1 | 10/2003 | Carlson | 138/129 |
| 2007/0137646 A1 * | 6/2007 | Weinstein et al. | 128/204.17 |

FOREIGN PATENT DOCUMENTS

| | | | |
|---|---|---|---|
| EP | 1 369 141 A1 | 12/2003 | A61M 16/08 |
| WO | WO 01/30431 A1 | 5/2001 | A61M 16/04 |
| WO | WO 2004/030527 * | 4/2004 | A61B 1/012 |
| WO | WO 2004/030527 A1 | 4/2004 | A61B 1/012 |

OTHER PUBLICATIONS

International Search Report with Written Opinion PCT/US2007/079713, 13 pages, Mar. 20, 2008.

* cited by examiner

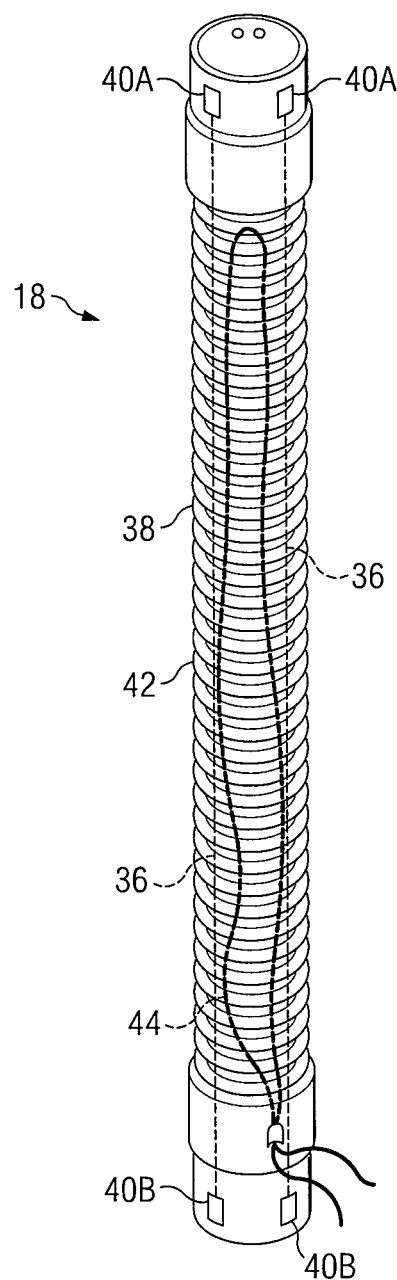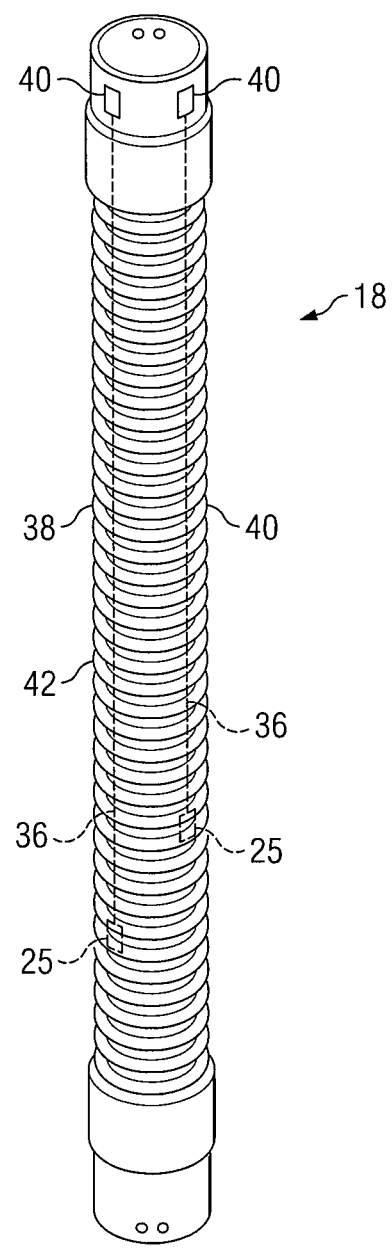

PATIENT INTERFACE HAVING AN INTEGRATED SYSTEM FOR COMMUNICATING DATA TO A VENTILATOR

TECHNICAL FIELD

The present disclosure relates generally to the field of medical devices, e.g., a patient interface having an integrated system for communicating data to a ventilator.

BACKGROUND

Conventional breathing assistance systems typically include a gas delivery system, a patient interface to deliver gas to one or more breathing passages of the patient, and a connection system between the gas delivery system and the patient interface. Such breathing assistance systems may be used, e.g., for mechanical ventilation of a patient's lungs and/or treatment of an apnea or other medical condition.

Calibration and operation of such breathing assistance systems may depend on the physical characteristics (e.g., geometric dimensions) of the various system components, vital statistics of the patient, atmospheric conditions in the treatment area and/or any other relevant parameters. Traditional implementation may include programming by a technician or other personnel and/or may include dedicated system components which are preset to interface with a limited number of alternative components.

Typically, a patient interface includes a patient end configured for insertion into or otherwise interfacing with one or more breathing passageways of a patient and a connection end configured for receiving gas communicated by a gas delivery apparatus and delivering gas to the patient. One example of a patient interface is an endotracheal tube including a tube portion and an inflatable cuff coupled to the tube portion. The inflatable cuff may provide a seal against escaping gas after the tube is inserted into a patient's breathing passageway, such as through a tracheostomy, nose and/or mouth. Another example of a patient interface is a mask sealed to the patient's mouth and/or nose.

SUMMARY

In accordance with one embodiment of the present disclosure, a medical device may include a patient interface for use in a breathing assistance system, an electronic device coupled to the patient interface, and one or more electrical conductors at least partially integrated with the patient interface. The patient interface may include a connection end configured for receiving gas communicated by a gas delivery apparatus, and a patient end configured for insertion into or more breathing passageways of a patient. The one or more electrical conductors at least partially integrated with the patient interface may be capable of facilitating communication of electrical signals between the electronic device and the gas delivery apparatus when the patient interface is communicatively coupled to the gas delivery apparatus.

In accordance with another embodiment of the present disclosure, a medical device may include patient interfacing means, signal producing means coupled to the patient interface means, and conducting means at least partially integrated with the patient interfacing means. The patient interfacing means may be configured for interfacing with a patient to deliver gas to the patient and may include a connection end configured for receiving gas communicated by a gas delivery means and a patient end configured for insertion into or more breathing passageways of the patient. The signal producing means may be configured for producing electrical signals, the signal producing means. The conducting means may be configured for facilitating communication of electrical signals between the signal producing means and the gas delivery means when the patient interfacing means is communicatively coupled to the gas delivery means.

In accordance with another embodiment of the present disclosure, a system may include a gas delivery apparatus, a connection interface, and a gas delivery control system. The gas delivery apparatus may be configured to communicate gas toward a patient. The connection interface may provide a physical interface for communicatively coupling the gas delivery apparatus to a patient interface such that gas may be delivered from the gas delivery apparatus to the patient interface. The connection interface may also provide an electrical interface for receiving electrical signals communicated by an electronic device at least partially integrated with the patient interface. The gas delivery control system may be configured to receive electrical signals from the electronic device via the connection system interface, and control a function of the gas delivery apparatus based at least on the electrical signals received from the electronic device.

In accordance with another embodiment of the present disclosure, a medical device may include a gas delivery apparatus configured to deliver gas toward a patient, a patient interface communicatively coupled to the gas delivery apparatus, an electronic device coupled to the patient interface and configured to produce electrical signals, and an electrical circuit extending between the patient interface and the gas delivery apparatus. The electrical circuit may be configured to communicate electrical signals between the electronic device and the gas delivery apparatus, and may include one or more electrical conductors at least partially integrated with the patient interface.

In accordance with another embodiment of the present disclosure, a method of communicating data in a breathing assistance system may include operating a system including a patient interface, an electronic device coupled to the patient interface, and one or more electrical conductors at least partially integrated with the patient interface. The patient interface may including a connection end configured for receiving gas communicated by a gas delivery apparatus, and a patient end configured for insertion into or more breathing passageways of a patient. The one or more electrical conductors may be capable of facilitating communication of electrical signals between the electronic device and the gas delivery apparatus when the patient interface is communicatively coupled to the gas delivery apparatus. The method may further include communicating electrical signals between the electronic device and the gas delivery apparatus via the one or more electrical conductors.

BRIEF DESCRIPTION OF THE DRAWINGS

Some embodiments of the disclosure may be understood by referring, in part, to the following description and the accompanying drawings wherein:

FIG. 2A illustrates an example connection system having one or more integrated electrical conductors for communicating electrical signals between a patient interface and a gas delivery apparatus, according to one embodiment of the present disclosure;

FIG. 2B illustrates an example connection system having one or more integrated electrical conductors for communicating electrical signals between electronic devices integral with the connection system and a gas delivery apparatus, according to one embodiment of the present disclosure;

DETAILED DESCRIPTION OF THE DRAWINGS

Selected embodiments of the disclosure may be understood by reference, in part, to FIGS. 1-9, wherein like numbers refer to same and like parts. The present disclosure is broadly concerned with breathing assistance systems (e.g., ventilators, CPAP systems, or BiPAP systems) adapted to be connected to one or more passageways (e.g., the mouth, nose, trachea and/or pharynx) of a patient to provide breathing assistance (e.g., providing ventilation and/or treating an apnea or other breathing condition) to a patient.

In some embodiments, the system may include a system for communicating electrical signals between various system components. For example, a breathing assistance system may include a gas delivery apparatus (e.g., a ventilator, CPAP device, or BiPAP device), a patient interface (e.g., a tracheal tube or a mask), a connection system (e.g., a single-limb or a dual-limb breathing circuit) between the gas delivery apparatus and the patient interface, and an electrical circuit (e.g., one or more wires and/or other conductors) extending from the patient interface, through the connection system, and to the gas delivery apparatus for communicating electrical signals between the patient interface and the gas delivery apparatus. In some embodiments, the electrical circuit may include one or more electrical conductors integral with the patient interface and/or one or more electrical conductors integral with the connection system.

In another embodiment, a patient interface (e.g., a tracheal tube or a mask) for use in a breathing assistance system may include a connection end configured for receiving gas communicated by a gas delivery apparatus (e.g., a ventilator, CPAP device, or BiPAP device), and a patient end configured for insertion into one or more breathing passageways of a patient (e.g., trachea, nose and/or mouth). An electronic device may be integrated with or otherwise coupled to the patient interface, and one or more electrical conductors may be at least partially integrated with the patient interface for facilitating communication of electrical signals between the electronic device and the gas delivery apparatus.

Figure 1:
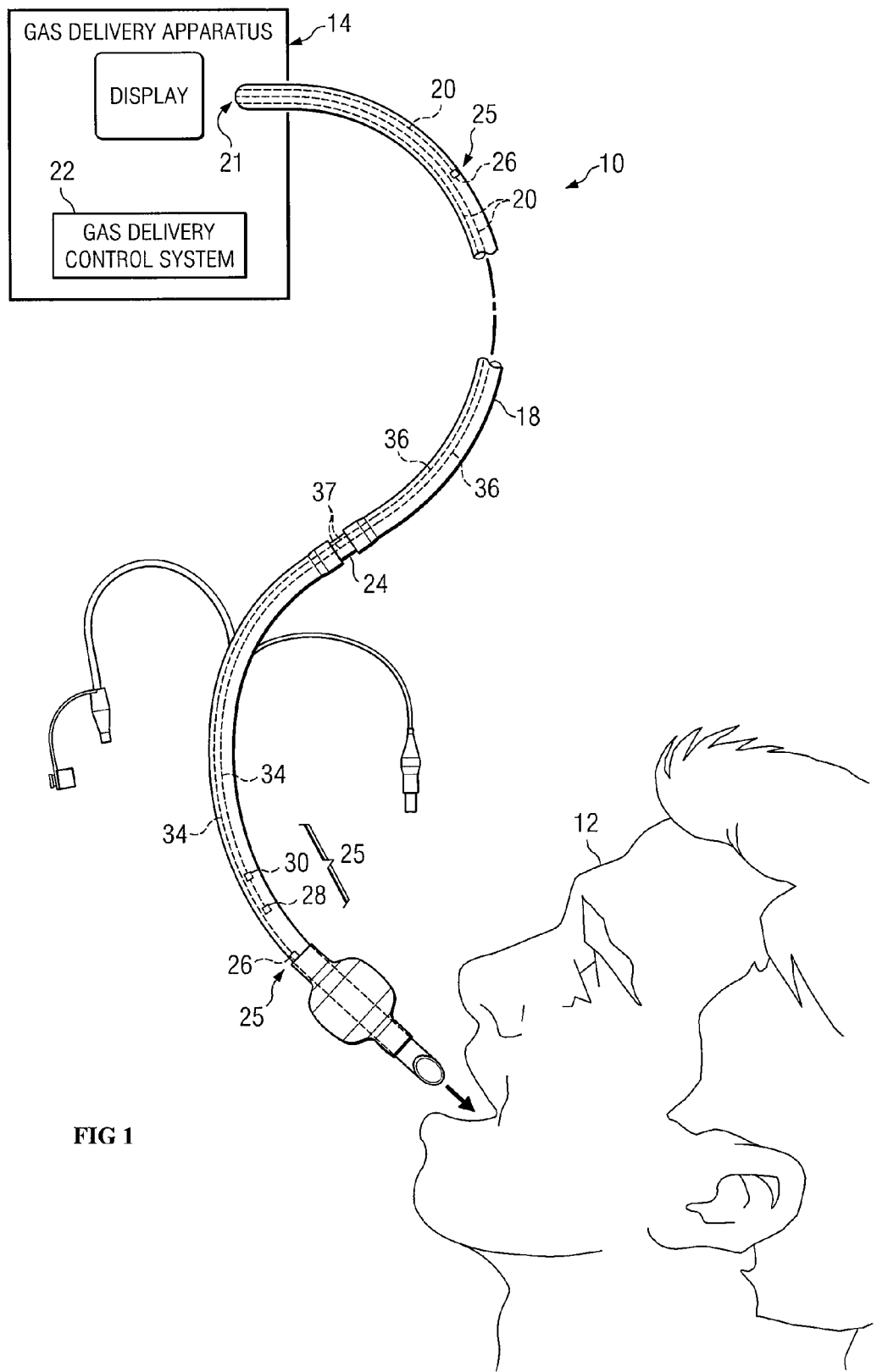
FIG. 1 illustrates an example breathing assistance system having one or more integrated electrical circuits for communicating electrical signals, according to one embodiment of the present disclosure.

FIG. 1 illustrates an example breathing assistance system 10 for providing breathing assistance to a patient 12, according to one embodiment of the disclosure. Breathing assistance system 10 may be generally configured to provide breathing assistance (e.g., providing ventilation and/or treating an apnea or other breathing condition) to a patient 12. Breathing assistance system 10 may include a gas delivery apparatus 14, a patient interface 16, a connection system 18 between gas delivery apparatus 14 and patient interface 16, and an integrated electrical circuit 20 for communicating electrical signals between connection system 18 and gas delivery apparatus 14 and/or between patient interface 16 and gas delivery apparatus 14.

Gas delivery apparatus 14 may include any device or devices configured to generate, supply, and/or deliver gas (e.g., pressurized air) toward patient 12 via patient interface 16. For example, gas delivery apparatus 14 may comprise a device capable of generating pressurized air (e.g., a ventilator, CPAP system, or BiPAP system), a wall outlet through which pressurized air may be supplied (e.g., in a hospital or clinic), one or more tanks of compressed gas, a compressor, or any other suitable source of pressurized or non-pressurized gas.

As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example. As used herein, the term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Gas delivery apparatus 14 may include an connection interface 21 configured to communicate gas toward a patient. For example, connection interface 21 may comprise a device capable of releasing gas to the atmosphere (e.g., a hole, a slit, a valve, and/or any other fluid passage), and/or a device capable of communicating gas from gas delivery apparatus 14 to connection system 18 or other tubes or conduits.

Gas delivery apparatus 14 may include a gas delivery control system 22 operable to control the breathing assistance provided by gas delivery apparatus 14 based on various input. For example, gas delivery control system 22 may regulate the pressure and/or flow of gas delivered to patient 12 based on various input (e.g., data received from sensors and/or input from a user). Gas delivery control system 22 may include, or have access to, one or more processors, memory devices, and any other suitable hardware or software. The one or more memory devices may store instructions (e.g., any suitable software, algorithms, or other logic or instructions that may be executed by one or more processors) for controlling the operation of gas delivery apparatus 14, e.g., controlling ventilation support provided by gas delivery apparatus 14.

Gas delivery apparatus 14 may further include any other components suitable for providing functionality related to providing breathing assistance to a patient 12. For example, gas delivery apparatus 14 may include one or more display devices for displaying various information regarding system 10 (e.g., data regarding patient 12, the operation of gas delivery apparatus 14, and/or any other relevant data), one or more sensors, a humidifier, a nebulizer, an alarm system, and/or any other suitable components.

Patient interface 16 may include any device or devices configured to interface with patient 12 to deliver gas to patient 12. For example, patient interface 16 may include a patient connection tube directly connected to the patient's trachea, an artificial airway (e.g., an endotracheal tube or other device) inserted in the patient's trachea, and/or a mask or nasal pillows positioned over the patient's nose and/or mouth. In embodiments including a patient connection tube, the patient connection tube may include a wye (or "Y") connector.

Connection system 18 may include any suitable means for connecting gas delivery apparatus 14 to patient interface 16. Connection system 18 may include one or more tubes, hoses, or other conduits suitable to communicate gas. Such tubes, hoses, or other conduits may be formed from any suitable materials, e.g., plastic, rubber, or other polymers, and may be generally flexible or generally rigid. For example, connection system 18 may comprise a breathing circuit including a flexible inspiration conduit and/or a flexible exhalation conduit. In some embodiments, connection system 18 may comprise a single-limb or a dual-limb breathing circuit.

When assembled, system 10 may define one or more gas delivery passageways from gas delivery apparatus 14, through connection system 18, and through patient interface 16. Such passageways may be used to deliver gas from gas delivery apparatus 14 to patient 12. In addition, in some embodiments, patient interface 16 and/or connection system 18 may include or define one or more passageways for communicating exhaled gas away from patient 12.

In some embodiments, system 10 may include one or more connectors 24 for connecting connection system 18 to gas delivery apparatus 14 and/or to patient interface 16. In some embodiments, connectors 24 may be removably attachable to gas delivery apparatus 14, patient interface 16, and/or connection system 18. In other embodiments, connection system 18 may be coupled directly to gas delivery apparatus 14 and patient interface 16 without such connectors 24.

System 10 may also include one or more electronic devices 25 coupled to patient interface 16, connection system 18, and/or connectors 24. Electronic devices 25 may include any devices capable of generating electrical signals, which signals may be communicated via one or more electrical circuits 20 (e.g., between patient interface 16 and gas delivery apparatus 14 or between connection system 18 and gas delivery apparatus 14). As examples only, electronic devices 25 may include one or more sensors 26, memory devices 28, and/or signal processors 30, each discussed below in greater detail. In some embodiments, one or more electronic devices 25 may be at least partially integrated with patient interface 16, connection system 18, and/or connectors 24. In other embodiments, one or more electronic devices 25 may be otherwise coupled to patient interface 16, connection system 18, and/or connectors 24.

Sensors 26 may include any device or devices for sensing, detecting, and/or monitoring one or more parameters related to the ventilation of patient 12, e.g., parameters regarding the ventilation provided by gas delivery apparatus 14 and/or physiological parameters regarding patient 12. For example, sensors 26 may include one or more devices for measuring various parameters of gas flowing into or out of patient 12 or gas delivery apparatus 14, e.g., the pressure, flow rate, flow volume, temperature, gas content, and/or humidity of such gas flow. Thus, sensors 26 may include, e.g., one or more pressure sensors, flow meters, transducers, and/or oxygen sensors. Sensors 26 may be located at one or more various locations in breathing assistance system 10 for monitoring the pressure and or flow of gasses flowing into and/or out of patient 12 and/or gas delivery apparatus 14. For example, one or more sensors 26 may be integrated with or located in or proximate gas delivery apparatus 14, connection system 18, and/or patient interface 16.

In some embodiments, one or more sensors 26 may be at least partially integrated with or otherwise coupled to patient interface 16, to provide access to patient parameters (e.g., core temperature, tracheal pressure, tissue pH, and/or other measurable parameters). For example, in embodiments in which patient interface 16 comprises a tracheal tube, an oro/naso tracheal tube and/or a mask, one or more sensors 26 (e.g., a thermistor, a pH electrode and/or a pressure transducer) may be integrated with or located in or proximate the tube or mask. Example configurations include, but are not limited to, sensors 26 integrated within a sidewall of patient interface 16, secured to the internal or external surface of a sidewall of patient interface 16, and/or attached or otherwise associated with any component of patient interface 16, connection system 18 and/or connectors 24.

Memory devices 28 may include any device or devices for recording and/or storing parameters related to the various components of connection system 18 or patient interface 16. For example, a memory device 28 may store physical and/or geometric parameters of one or more components of connection system 18 or patient interface 16 (e.g., values for an inner diameter and/or length of a component of connection system 18).

As another example, a memory device 28 may store an identifier (e.g., a serial number, device code and/or other code) for identifying the type (or the particular unit) of a particular connection system 18 or patient interface 16.

As another example, a memory device 28 may store data for identifying one or more other electronic devices 25 coupled to the particular connection system 18 or patient interface 16. For instance, a memory device 28 integrated in a patient interface 16 may store data indicating that patient interface 16 includes a flow sensor and a pressure sensor.

As another example, a memory device 28 may store data for identifying the number and or type(s) of data channels provided by the particular connection system 18 or patient interface 16. For instance, a memory device 28 integrated in a connection system 18 may store data indicating that the connection system 18 includes three data channels for communicating three channels of data between patient interface 16 and gas delivery apparatus 14.

In some embodiments, one or more memory devices 28 may be at least partially integrated with or otherwise coupled to patient interface 16, connection system 18 and/or connectors 24. For example, in embodiments in which patient interface 16 comprises a tracheal tube, an oro/naso tracheal tube and/or a mask, one or more memory devices 28 may be integrated with or located in or proximate the tube or mask. Example configurations include, but are not limited to, memory devices 28 integrated within a sidewall of patient interface 16, secured to the internal or external surface of a sidewall of patient interface 16, and/or attached or otherwise associated with any component of patient interface 16, connection system 18 and/or connectors 24.

Signal processors 30 may include any device or devices for processing signals received from one or more electrical devices 25 (e.g., one or more sensors 26 and/or one or more memory devices 28), e.g., converting analog signals to digital signals, and/or interpreting identifiers (e.g., serial numbers, device codes and/or other codes) of various components of connection system 18 or patient interface 16. For example, a signal processor 30 may include a device configured to interrogate one or more memory devices 28 and to generate signals indicating the results of such interrogation that may be communicated to gas delivery apparatus 14 via an integrated electrical circuit 20. As another example, a signal processor 30 may include a device configured to receive a signal generated by one or more sensors 26, analyze the received signal, and/or convert the signal to a format suitable for communication to gas delivery apparatus 14 (e.g., a format readable by gas delivery control system 22).

In some embodiments, one or more signal processors 30 may be located within or proximate gas delivery device 14, connection system 18 and/or patient interface 16. Example configurations include, but are not limited to, signal processors 30 integrated within a sidewall of patient interface 16, secured to the internal or external surface of a sidewall of patient interface 16, and/or attached or otherwise associated with any component of patient interface 16, connection system 18 and/or connectors 24.

As discussed above, system 10 may include one or more electrical circuits 20 for communicating electrical signals between connection system 18 and gas delivery apparatus 14 and/or between patient interface 16 and gas delivery apparatus 14. In some embodiments, one or more electrical circuits 20 may be configured to communicate signals from one or more sensors 26, memory devices 28, and/or signal processors 30 to gas delivery apparatus 14.

An electrical circuit 20 may comprise one, two, or more conductive pathways configured to communicate electrical signals between two points in either one direction or both directions. An electrical circuit 20 may include any number of electrically conductive elements (referred to herein as "conductors") connected to form a conductive pathway. For example, an electrical circuit 20 may include one or more patient interface conductors 34 at least partially integrated with patient interface 16, one or more connection system conductors 36 at least partially integrated with connection system 18, and/or one or more connector conductors 37 at least partially integrated with one or more connectors 24. An electrical circuit 20 may also include any other conductors for completing the circuit 20, e.g., one or more conductors integrated or otherwise associated with one or more connectors 24 between connection system 18 and to patient interface 16 and/or between connection system 18 and gas delivery apparatus 14. Each conductor may comprise any element operable to communicate electrical signals. For example, conductors may include wires (insulated or non-insulated), conductive vias, printed circuits and/or any other element that contains movable charges of electricity.

Patient interface conductors 34 may communicate electrical signals to and/or from one or more electronic devices (e.g., one or more sensors 26, memory devices 28, and/or signal processors 30), and may terminate in electrical contacts configured to mate with electrical contacts associated with connection system 18 and/or a connector 24 between patient interface 16 and connection system 18. As discussed above, patient interface conductors 34 may be at least partially integrated with patient interface 16. For example, a patient interface conductor 34 may be integrated or embedded within, or secured to an internal or external surface of, a sidewall of patient interface 16. As another example, a patient interface conductor 34 be integrated or embedded within an insulating tube or coating and may run within or coupled to patient interface 16. In some embodiments in which patient interface 16 comprises a tracheal tube, a patient interface conductor 34 may be integrated or embedded within a side wall of the tube, or may otherwise run along a length of the tube within the tube. Example embodiments are discussed in greater detail below with reference to FIGS. 3 and 4.

In some embodiments, connection system conductors 36 may communicate electrical signals from a first end of connection system 18 to a second end of connection system 18 in order to support communications between patient interface 16 and gas delivery apparatus 14. In such embodiments, connection system conductors 36 may terminate in first electrical contacts proximate a first end of connection system 18 and in second electrical contacts proximate a second end of connection system 18, as discussed in greater detail below with reference to FIG. 2A.

In embodiments in which connection system 18 includes one or more electronic devices 25 (e.g., one or more sensors 26, memory devices 28, and/or signal processors 30), connection system conductors 36 may communicate electrical signals to and/or from such electronic devices 25. In such embodiments, a connection system conductor 36 may extend from an electronic device 25 and terminate in an electrical contact proximate one end of connection system 18, as discussed in greater detail below with reference to FIG. 2B.

As discussed above, connection system conductors 36 may be at least partially integrated with connection system 18. For example, a connection system conductor 36 may be integrated or embedded within, or secured to an internal or external surface of, a sidewall of connection system 18. As another example, a connection system conductor 36 may be integrated or embedded within an insulating tube or coating and may run within or coupled to connection system 18. In some embodiments in which connection system 18 comprises a breathing circuit, a connection system conductor 36 may be integrated or embedded within a side wall of the inspiration conduit and/or exhalation conduit, or may otherwise run along a length of and within the inspiration conduit and/or exhalation conduit. Example embodiments are discussed in greater detail below with reference to FIGS. 2A and 2B.

As discussed above, gas delivery control system 22 may be operable to control the ventilation support provided by gas delivery apparatus 14 based on various input. Such input may include input received from an operator (e.g., via a touch screen and/or other user interfaces provided by gas delivery apparatus 14) and/or data received from one or more electronic devices 25 (e.g., sensors 26, memory devices 28, and/or signal processors 30) via one or more electrical circuits 20. For example, gas delivery control system 20 may regulate the pressure, flow, and/or any other parameter of breathing gas delivered to patient 12 based at least on a signal received via one or more electrical circuits 20 from one or more sensors 26, e.g., data regarding pressure, flow, temperature, humidity, pH, and/or any other relevant parameter. As another example, gas delivery control system 20 may regulate the pressure, flow, and/or any other parameter of breathing gas delivered to patient 12 based at least on a signal received via one or more electrical circuits 20 from one or more memory devices 28, e.g., data identifying various physical or other characteristics of the patient interface 16 or connection system 18. As another example, gas delivery control system 20 may regulate the pressure, flow, and/or any other parameter of breathing gas delivered to patient 12 based at least on a signal received via one or more electrical circuits 20 from one or more signal processors 30 (e.g., data identifying various physical or other characteristics of the patient interface 16 or connection system 18 and/or data regarding pressure, flow, temperature, humidity, pH, and/or any other relevant parameter).

Connection interface 21 of gas delivery apparatus 14 may by configured to provide both (a) a physical interface (e.g., a physical outlet) for coupling connection system 18 to gas delivery apparatus 14 (thus communicatively coupling patient interface 16 to gas delivery apparatus 14), and (b) an electrical interface for connecting one or more connection system conductors 36 to internal components of gas delivery apparatus 14 (e.g., gas delivery control system 22). The electrical interface may thus be configured for communicating electrical signals between internal components of gas delivery apparatus 14 (e.g., gas delivery control system 22) and one or more electronic devices 25 via one or more integrated electrical circuits 20. For example, gas delivery control system 22 may receive signals from an electronic device 25 via an integrated electrical circuit 20 and connection interface 21, and control one or more functions of gas delivery apparatus 14 (e.g., the pressure, flow, and/or other parameter of gas delivered by gas delivery apparatus 14) based at least on the received electrical signals.

FIG. 2A illustrates an example connection system 18 having one or more integrated connection system conductors 36 for communicating signals between gas delivery apparatus 14 and patient interface 16, according to one embodiment of the present disclosure. Connection system 18 may define a conduit capable of communicating gas between gas delivery apparatus 14 and patient interface 16. For instance, in certain embodiments, connection system 18 may include one or more hoses 38 having a side wall 42. Hoses may be generally flexible or rigid, and may be formed from any suitable materials, e.g., plastic, rubber, or other polymers. In such embodiments, one or more connection system conductors 36 configured to communicate electrical signals between patient interface 16 and gas delivery apparatus 14 may be embedded and/or otherwise integral with side wall 42 for at least a portion of the length of connection system 18. In some embodiments, one or more connection system conductors 36 may be embedded and/or otherwise integral with side wall 42 for the complete length of connection system 18 (i.e., from a first end to a second end of connection system 18). As another example, one or more connection system conductors 36 may be integrated or embedded within an insulating tube running within or coupled to connection system 18.

In embodiments that include connection system conductors 36 and any other conductors appropriate to complete integrated electrical circuit 20, connection system 18 may include additional components operable to complete integrated electrical circuit 20. For example, as shown in FIG. 2A, connection system conductors 36 may terminate in first electrical contacts 40A proximate a first end of connection system 18 and in second electrical contacts 40B proximate a second end of connection system 18. Electrical contacts 40A may be configured to connect to corresponding electrical contacts associated with patient interface 16 (or with a connector 24 between connection system 18 and patient interface 16) to provide an electrical connection between connection system 18 and patient interface 16. Electrical contacts 40B may be configured to connect to corresponding electrical contacts associated with gas delivery apparatus 14 (or with a connector 24 between connection system 18 and gas delivery apparatus 14) to provide an electrical connection between connection system 18 and gas delivery apparatus 14. In some embodiments, electrical contacts 40A and or 40B may be positioned around the perimeter of either end of hose 38.

In some embodiments, connection system 18 may also include one or more heating conductors 44 that may be configured to heat the gas flowing through connection system 18, e.g., to prevent or reduce condensation from humidified gases. In other embodiments, connection system 18 may not include such heating conductors 44.

FIG. 2B illustrates an example connection system 18 having one or more integrated connection system conductors 36 for communicating signals between one or more electronic devices 25 (e.g., sensors 26, memory devices 28, and/or signal processors 30) and gas delivery apparatus 14, according to one embodiment of the present disclosure. Connection system conductors 36 may be embedded and/or otherwise integral with side wall 42 for at least a portion of the length of connection system 18. In some embodiments, one or more connection system conductors 36 may be embedded and/or otherwise integral with side wall 42 for the complete length extending from the relevant electronic devices 25 to one end of connection system 18. As another example, one or more connection system conductors 36 may be integrated or embedded within an insulating tube running within or coupled to connection system 18.

Each connection system conductor 36 may terminate in an electrical contact 40 proximate one end of connection system 18. Electrical contacts 40 may be configured to connect to corresponding electrical contacts associated with gas delivery apparatus 14 (or with a connector 24 between connection system 18 and gas delivery apparatus 14) to provide an electrical connection between connection system 18 and gas delivery apparatus 14. In some embodiments, electrical contacts 40 may be positioned around the perimeter of the end of hose 38.

Figure 3:
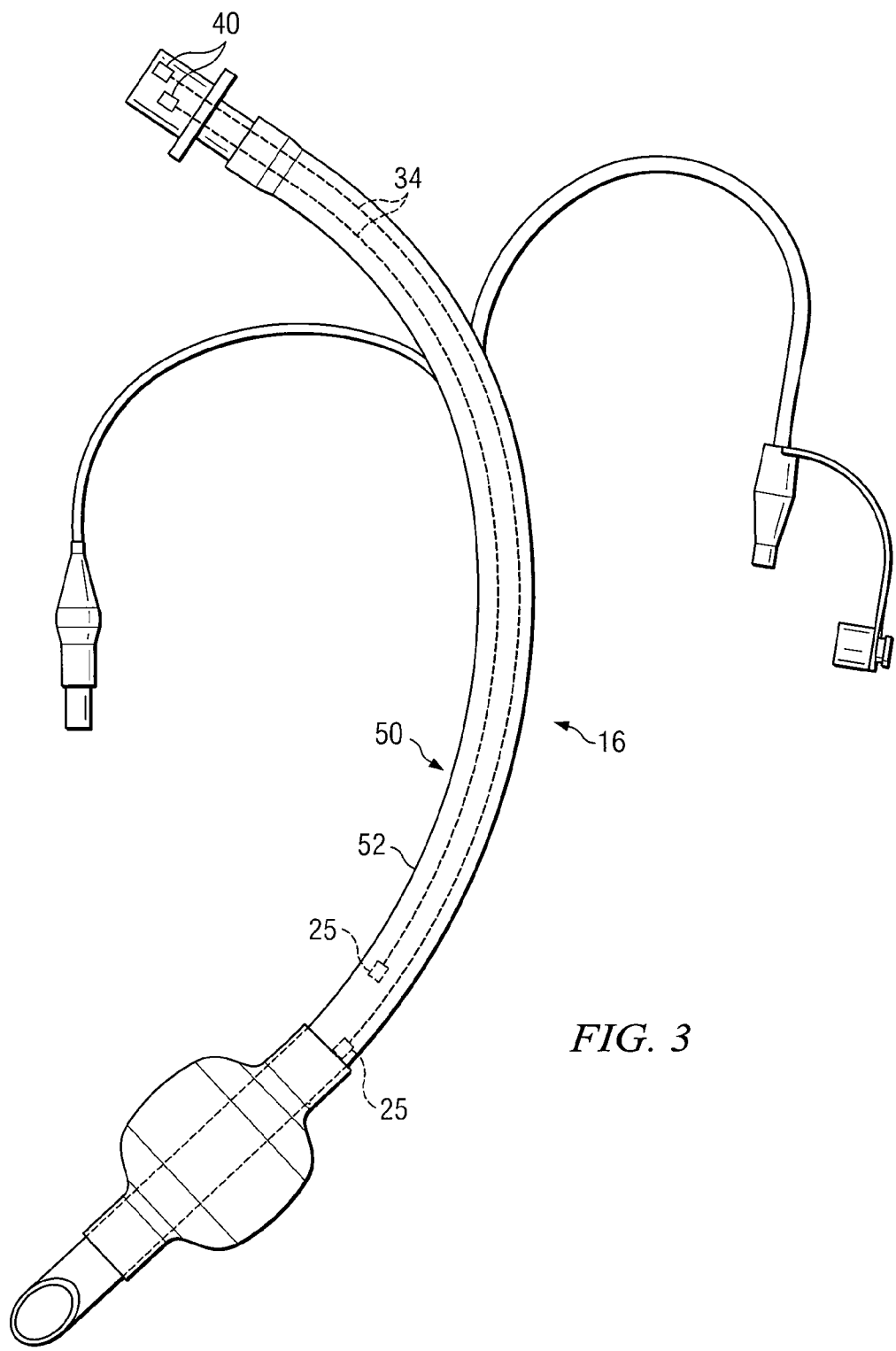
FIG. 3 illustrates an example tracheal tube having one or more integrated electrical conductors and one or more integrated electronic devices, according to one embodiment of the present disclosure.

FIG. 3 illustrates an example embodiment of patient interface 16 in which patient interface 16 is a tracheal tube. Tracheal tube 16 may include one or more integral patient interface conductors 34 for communicating signals to and/or from one or more electronic devices 25 (e.g., sensors 26, memory devices 28, and/or signal processors 30) integral with tracheal tube 16.

Tracheal tube 16 may include tubular body 50 having at least one side wall 52. Tube 16 may include a connection end 54 configured for receiving gas from gas delivery apparatus 14, and a patient end 56 configured for insertion into one or more breathing passageways of patient 12. In some embodiments, one or more patient interface conductors 34 may be embedded in or otherwise integral with side wall 52. As another example, one or more patient interface conductors 34 may be integrated or embedded within an insulating tube running within or coupled to tubular body 50. Patient interface conductors 34 may run from one or more electronic devices 25 integral with or otherwise associated with tube 16, and may terminate in one or more electrical contacts 40 proximate an end of tube 16. Electrical contacts 40 may be configured to connect to corresponding electrical contacts associated with connection system 18 (or with a connector 24 between connection system 18 and tube 16) to provide an electrical connection between tube 16 and connection system 18. In some embodiments, electrical contacts 40 may be positioned around the perimeter of the end of tube 16.

Figure 4:
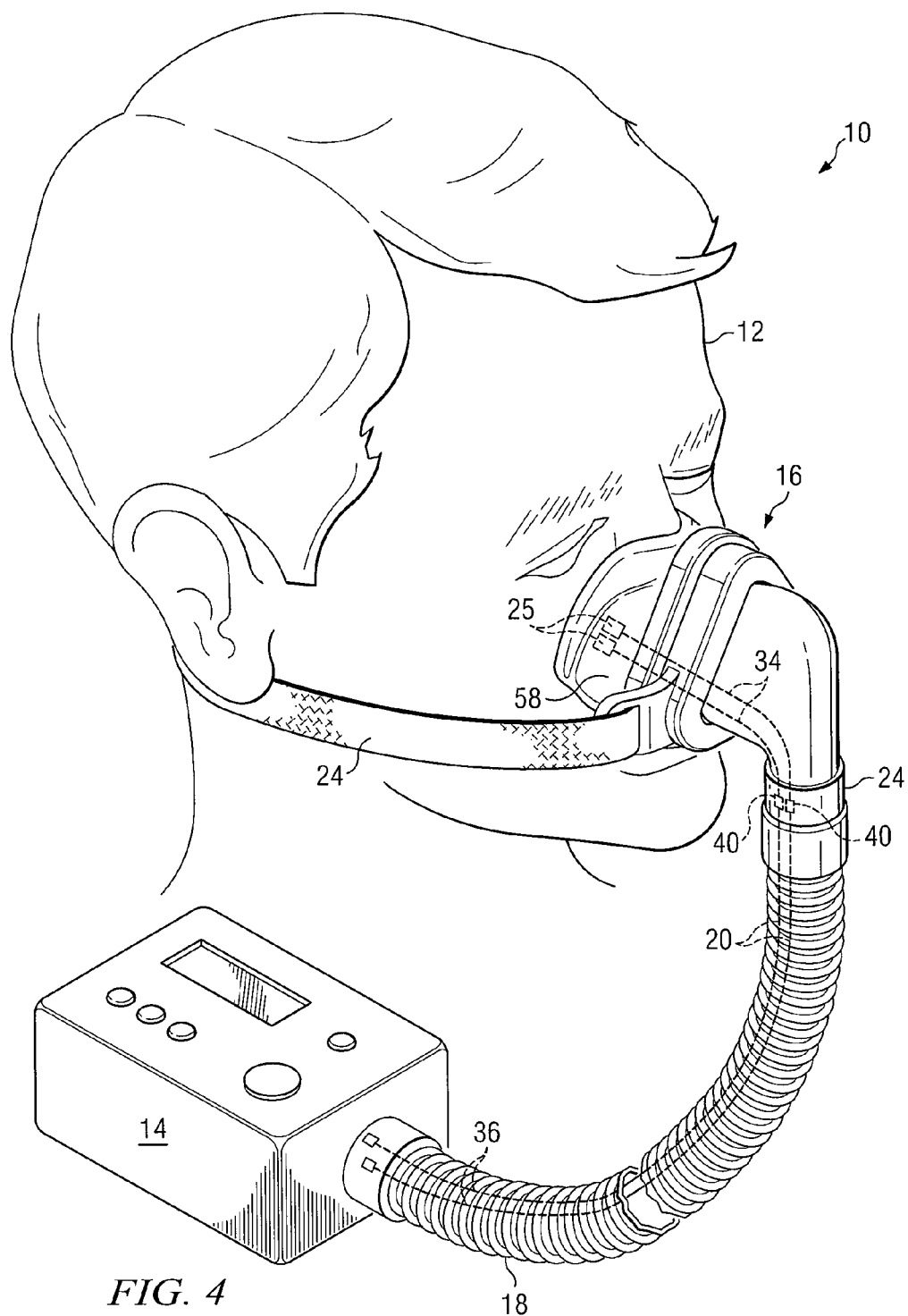
FIG. 4 illustrates an example patient mask having one or more integrated electrical conductors and one or more integrated electronic devices, according to another embodiment of the present disclosure.

FIG. 4 illustrates an example embodiment of patient interface 16 in which patient interface 16 is a mask. Mask 16 may include one or more integral patient interface conductors 34 for communicating signals to and/or from one or more electronic devices 25 (e.g., sensors 26, memory devices 28, and/or signal processors 30) integral with mask 16.

Mask 16 may comprise any type of mask or other facial interface for delivering gas to patient 12, e.g., a nasal mask, a mouth mask, a face mask covering both the nose and mouth, and/or nasal pillows. Mask 16 may include at least one side wall 58. In some embodiments, one or more patient interface conductors 34 may be embedded in or otherwise integral with one or more side walls 58. As another example, one or more patient interface conductors 34 may be integrated or embedded within an insulating tube running within or coupled to mask 16. Patient interface conductors 34 may run from one or more electronic devices 25 integral with or otherwise associated with mask 16 (e.g., one or more sensors 26, memory devices 28, and/or signal processors 30), and may terminate in one or more electrical contacts 40 proximate one side or end of mask 16. Electrical contacts 40 may be configured to connect to corresponding electrical contacts associated with connection system 18 (or with a connector 24 between connection system 18 and mask 16) to provide an electrical connection between mask 16 and connection system 18. In some embodiments, electrical contacts 40 may be positioned around the perimeter of the end of mask 16.

Figure 5:
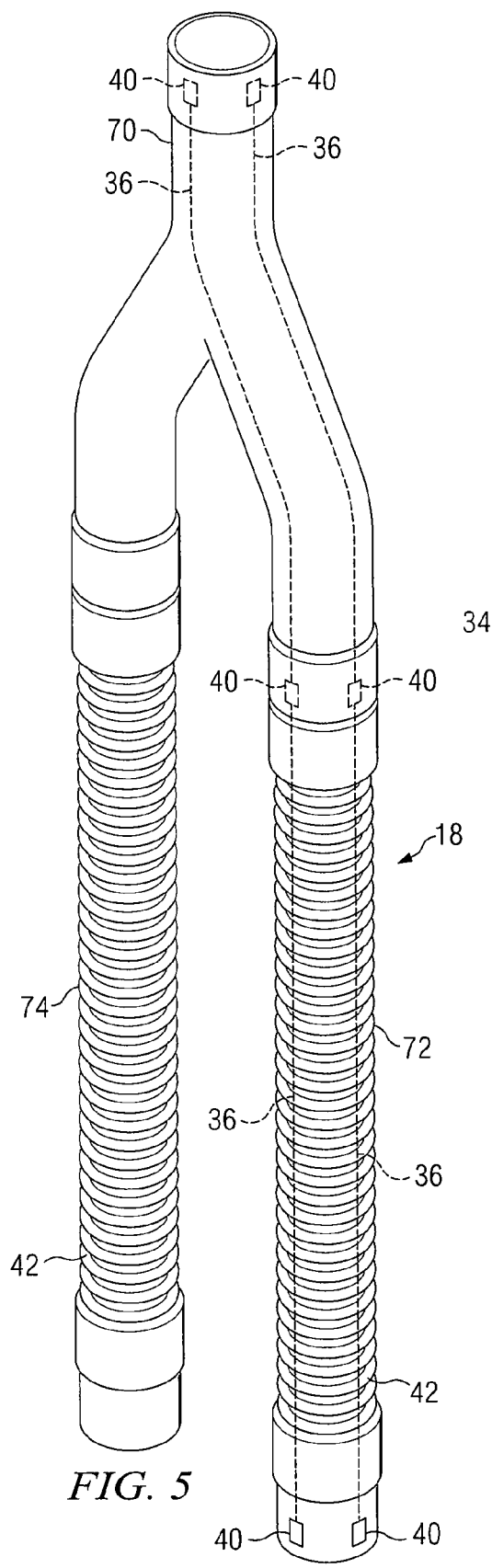
FIG. 5 illustrates an example breathing assistance system including a dual-limb connection system, according to one embodiment of the present disclosure.

FIG. 5 illustrates an example breathing assistance system 10 including a dual-limb connection system 18, according to one embodiment of the present disclosure. In this embodiment, connection system 18 comprises a dual-limb breathing circuit including an inspiration conduit 72, an exhalation conduit 74, and a wye ("Y") connector 70 configured to attach breathing circuit 18 to patient interface 16. In some embodiments, such as that shown in FIG. 5, connection system 18 may include one or more connection system conductors 36 embedded in or otherwise integral with one or more side walls 42 of inspiration conduit 72 and/or connector 70. In other embodiments, connection system 18 may include one or more conductors 36 embedded in or otherwise integral with one or more side walls 42 of exhalation conduit 74. In other embodiments, connection system 18 may include one or more conductors 36 embedded in or otherwise integral with one or more side walls 42 of inhalation conduit 72 and one or more conductors 36 embedded in or otherwise integral with one or more side walls 42 of exhalation conduit 74.

Figure 6:
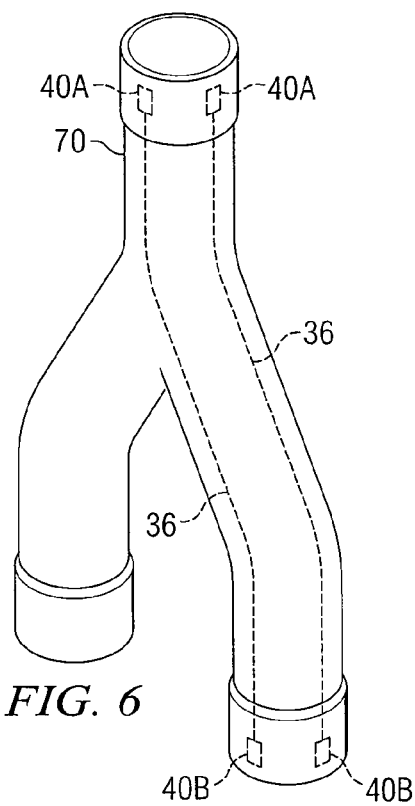
FIG. 6 illustrates an example "Y" connector for a dual-limb connection system and having one or more integrated electrical conductors, according to one embodiment of the present disclosure.

FIG. 6 illustrates an example wye connector 70 for a dual-limb breathing circuit 18, according to one embodiment of the present disclosure. Wye connector 70 may be separate from and removably attachable to breathing circuit 18. Wye connector 70 may include one or more passages through which gas may pass from connection system 18 to patient interface 16. Wye connector 70 may include one or more connection system conductors 36 at least partially integral to wye connector 70. In certain embodiments, such as that shown in FIG. 6, wye connector 70 may include one or more conductors 36 that terminate in first electrical contacts 40A proximate a first side or end of wye connector 70 and in second electrical contacts 40B proximate a second side or end of wye connector 70. Electrical contacts 40A may be configured to connect to corresponding electrical contacts associated with patient interface 16 (or with a connector 24 between wye connector 70 and patient interface 16) to provide an electrical connection between wye connector 70 and patient interface 16. Electrical contacts 40B may be configured to connect to corresponding electrical contacts associated with breathing circuit 18 (e.g., inspiration conduit 72 and/or exhalation conduit 74) to provide an electrical connection between wye connector 70 and breathing circuit 18. In some embodiments, electrical contacts 40A and or 40B may be positioned around the perimeter of either end of wye connector 70.

In some embodiments, connection system conductors 36 may terminate in electrical connectors. Electrical connectors may include any structure or device operable to connect electrical conductors of connected components of system 10. For example, electrical connectors may be used to connect conductors 34, 36, and/or 37 or corresponding patient interface 16, connection system 18, and/or connectors 24. Example electrical connectors may include, e.g., wire nuts, terminals, terminal blocks, banana plugs, crimp-on terminals, lugs, plug and socket connectors, DIN connector, D-subminiature plugs, registered jack and/or any other suitable connectors. Example embodiments are discussed below with reference to FIGS. 7 and 8.

Figure 7:
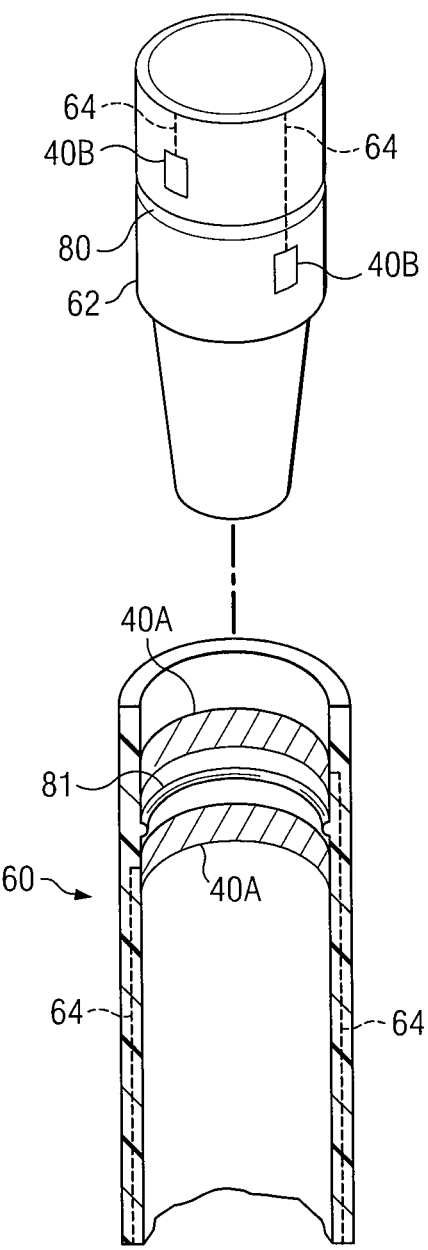
FIG. 7 illustrates example physical alignment keys for aligning electrical contacts of different components of a breathing assistance system, according to one embodiment of the present disclosure.
Figure 8:
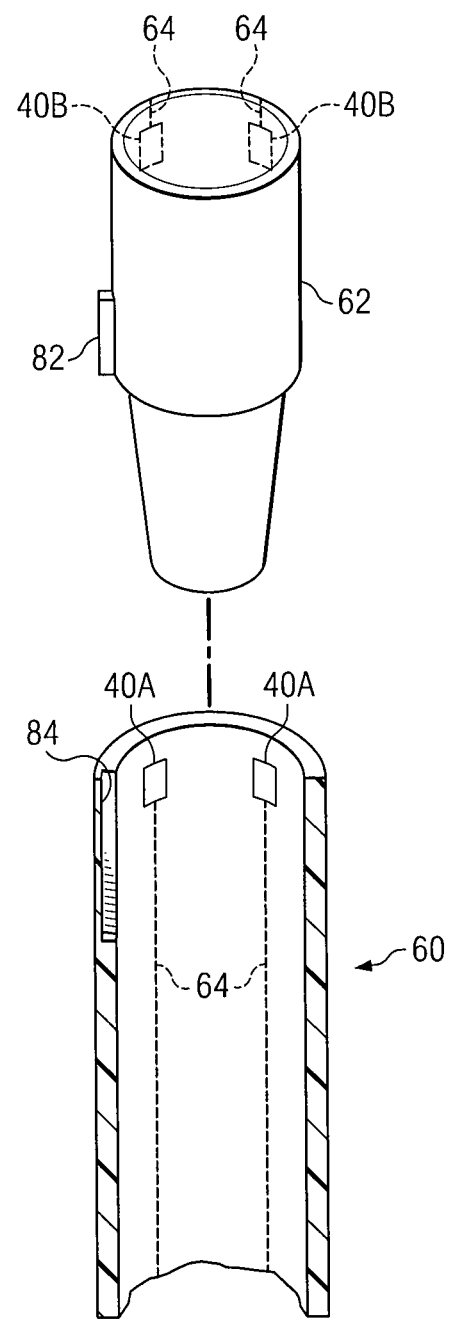
FIG. 8 illustrates example physical alignment keys for aligning electrical contacts of different components of a breathing assistance system, according to another embodiment of the present disclosure.

FIGS. 7 and 8 illustrates example physical alignment keys for aligning and/or connecting electrical conductors of different components of a breathing assistance system 10, according to one embodiment of the present disclosure. More particularly, FIGS. 7 and 8 illustrate an example joint between a first system component 60 and a second system component 62 that includes physical alignment keys which may be configured to ensure proper electrical between electrical conductors 64 integrated in or coupled to each of the two components 60 and 62. System components 60 and 62 may be any components of system 10, e.g., connection interface 21 of gas delivery apparatus 14, connection system 18, patient interface 16, and/or connectors 24. Electrical conductors 64 may comprise any portion of an integrated electrical circuit 20, e.g., conductors 34, 36, and/or 37.

Electrical conductors 64 of first system component 60 may terminate in electrical contacts 40A, and electrical conductors 64 of second system component 62 may terminate in electrical contacts 40B. Physical alignment keys may be any physical feature of system component 60 and/or system component 62 that restricts relative alignment between the two system components in any one or more direction such that electrical contacts 40A and 40B physically contact each other when components 60 and 62 are connected.

For example, physical alignment keys may be provided to align contacts 40A and 40B in an axial direction to ensure physical contact between contacts 40A and 40B when components 60 and 62 are connected. For example, as shown in FIG. 7, system component 62 may include an insertion depth key slot 80. System component 60 may include a ridge 81 positioned to engage insertion depth key slot 80 to fix the depth of insertion of component 62 into component 60. In such embodiments, electrical contacts 40B on system component 62 may be located at a predetermined physical distance from the end of component 62, and electrical contacts 40A on component 60 may be located so that electrical contacts 40A and electrical contacts 40B are in physical contact when component 62 is fully inserted into component 60. Insertion depth key slot 80 and ridge 81 may have any suitable physical dimension or configuration and may be located at any position on components 60 and/or 62 such that they are configured to ensure physical contact between electrical contacts 40A electrical contacts 40B when components 60 and 62 are joined.

As another example, physical alignment keys may be provided to align contacts 40A and 40B in a radial or rotational direction to ensure physical contact between contacts 40A and 40B when components 60 and 62 are connected. For example, as shown in FIG. 8, system component 62 may include a tongue 82 and system component 60 may include a groove 84 configured to receive tongue 82. Tongue 82 and groove 84 may function as physical structures capable of fixing the relative rotational alignment between components 60 and 62. Electrical contacts 40B may be located at a predetermined angle from tongue 82 and electrical contacts 40A may be located at a corresponding predetermined angle from groove 84. The angles may be chosen so that electrical contacts 40A and electrical contacts 40B physically contact each other when tongue 82 is fully inserted into groove 84 (i.e., when components 60 and 62 are connected). Tongue 82 and groove 84 may have any suitable physical dimension or configuration and may be located at any position on components 60 and/or 62 such that they are configured to ensure physical contact between electrical contacts 40A electrical contacts 40B when components 60 and 62 are joined.

In some embodiments, a connection between two system components 60 and 62 may include both physical alignment keys for aligning contacts 40A and 40B in an axial direction (e.g., as shown in FIG. 7) and physical alignment keys for aligning contacts 40A and 40B in a radial or rotational direction (e.g., as shown in FIG. 8). In other embodiments, any other suitable alignment keys or other systems may be used to ensure connection between contacts 40 of connected components of system 10.

Figure 9:
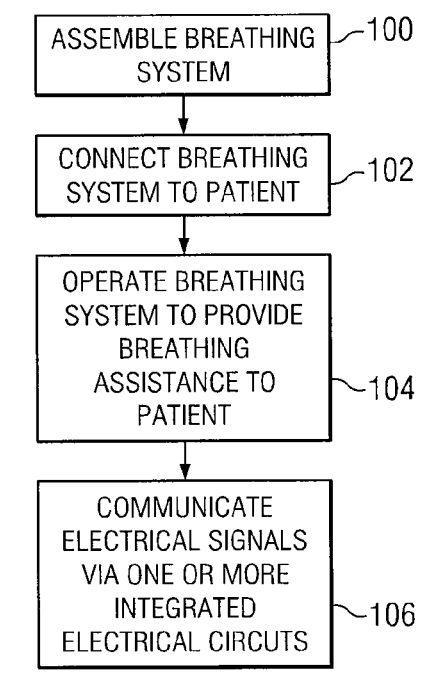
FIG. 9 illustrates an example gas delivery apparatus including an output port, a connection component, and a logic control unit, according to another embodiment of the present disclosure.

FIG. 9 is a flowchart illustrating a method of using integrated electrical circuits 20 to communicate data through a breathing assistance system 10, according to one embodiment of the present disclosure. At step 100, breathing assistance system 10 may be assembled, which may include connecting gas delivery system 14, connection system 18, patient interface 16, any connectors 24, and/or any other components of system 10. The assembled system 10 may define one or more pathways for communicating gas between gas delivery apparatus 14 and patient interface 16, and one or more integrated electrical circuits 20 for communicating electrical signals between patient interface 16 and gas delivery apparatus 14 and/or between connection system 18 and gas delivery apparatus 14.

At step 102, breathing assistance system 10 may be connected to a patient 12, which may include securing patient interface 16 (e.g., a tracheal tube or mask) to patient 12. At step 104, breathing assistance system 10 may be operated to provide breathing assistance to patient 12 (e.g., providing ventilation and/or treating an apnea or other breathing condition). At step 106, electrical signals may be communicated via the one or more integrated electrical circuits 20, e.g., to communicate data between one or more electronic devices 25 (e.g., sensors 26, memory devices 28, and/or signal processors 30) and gas delivery apparatus 14. Such signals may be used in any suitable manner, e.g., such signals may be used by gas delivery control system 22 to control the operation of gas delivery apparatus 14.

It will be appreciated that while the disclosure is particularly described in the context of breathing assistance systems, the apparatuses, techniques, and methods disclosed herein may be similarly applied in other contexts. For example, similar principles may be applied to a variety of other surgical and/or medical fluid delivery and/or monitoring devices, e.g., intravenous pumps, gastronomy tubes and/or catheters. Additionally, it should be understood that various changes, substitutions and alterations can be made herein without departing from the spirit and scope of the disclosure as illustrated by the following claims.

What is claimed is:

1. A medical device, comprising:
a patient interface device for use in a breathing assistance system, the patient interface device including:
a connection end configured to receive gas communicated by a gas delivery apparatus, the connection end having a plurality of contacts; and
a patient end configured to be inserted into one or more breathing passageways of a patient;
a plurality of electronic devices embedded within a sidewall of the patient interface device proximate the patient end, the plurality of electronic devices configured to generate electrical signals and comprising at least one memory device and at least one signal processor, wherein the at least one signal processor is physically separate from the at least one memory device and is configured to process signals received from the at least one memory device; and
one or more electrical conductors at least partially embedded within the sidewall of the patient interface device, the one or more electrical conductors coupling the plurality of electronic devices to the plurality of contacts to facilitate communication of the electrical signals from the one or more electronic devices to the gas delivery apparatus when the patient interface device is communicatively coupled to the gas delivery apparatus.

2. A medical device according to claim 1, wherein the one or more electrical conductors define a portion of an electrical circuit between the plurality of electronic devices and the gas delivery apparatus when the patient interface device is communicatively coupled to the gas delivery apparatus.

3. A medical device according to claim 1, comprising one or more sensors at least partially embedded within the sidewall of the patient interface device, wherein the one or more sensors are physically separate from the at least one signal processor.

4. A medical device according to claim 3, wherein the one or more sensors are configured to produce electrical signals corresponding to one or more patient parameters.

5. A medical device according to claim 3, wherein the one or more sensors are configured to produce electrical signals corresponding to one or more parameters regarding gas flowing through the patient interface device.

6. A medical device according to claim 1, wherein the plurality of contacts comprise a plurality of electrical connectors proximate the connection end of the patient interface device.

7. A medical device according to claim 1, wherein the connection end of the patient interface device is configured to connect to, and to receive gas from, a connection system configured to transfer gas from the gas delivery device to the patient interface device.

8. A medical device according to claim 7, wherein
the connection end of the patient interface device is configured to complete an electrical connection between the one or more electrical conductors at least partially embedded within the sidewall of the patient interface device and one or more electrical conductors embedded within a sidewall of the connection system.

9. A medical device according to claim 1, wherein:
the connection end of the patient interface device is configured to receive gas from a connector configured to attach the patient interface device to one or more components of a connection system; and
the connection end of the patient interface device is configured to complete an electrical connection between the one or more electrical conductors at least partially embedded within the sidewall of the patient interface device and one or more electrical conductors embedded within a sidewall of the connector.

10. A medical device according to claim 1, comprising one or more circuitry components configured to produce electrical signals for communication via the one or more electrical conductors at least partially embedded within the sidewall of the patient interface device.

11. A medical device according to claim 1, wherein the patient interface device comprises an endotracheal tube having the sidewall.

12. A medical device according to claim 1, wherein the patient interface device comprises an orotracheal tube having the sidewall.

13. A medical device according to claim 1, wherein the patient interface device comprises a nasotracheal tube having the sidewall.

14. A medical device comprising:
  patient interfacing means for interfacing with a patient to deliver gas to the patient, the patient interfacing means being a physical device and including a connection end configured for receiving gas communicated by a gas delivery means and a patient end configured for insertion into one or more breathing passageways of the patient, the connection end having plurality of contacts;
  signal producing means for producing electrical signals, the signal producing means being embedded within a sidewall of the patient interfacing means proximate the patient end, wherein the signal producing means comprises at least one memory device and at least one signal processor, and wherein the at least one signal processor is physically separate from the at least one memory device and is configured to process signals received from the at least one memory device; and
  conducting means for facilitating communication of electrical signals between the signal producing means and the gas delivery means via the plurality of contacts when the patient interfacing means is communicatively coupled to the gas delivery means, the conducting means at least partially embedded within the sidewall of the patient interfacing means.

15. A system, comprising:
  gas delivery apparatus configured to communicate gas toward a patient;
  a connection interface configured to:
    provide a physical interface configured to communicatively couple the gas delivery apparatus to a patient interface device such that gas may be delivered from the gas delivery apparatus to the patient interface device, the patient interface device having a connection end configured to couple to the connection interface and a patient end configured to be disposed proximate the patient, the connection end having a plurality of contacts; and
    provide an electrical interface configured to receive electrical signals from a plurality of electronic devices embedded within a sidewall of the patient interface device proximate the patient end and electrically coupled to the plurality of contacts, wherein the plurality of electronic devices comprise at least one memory device and at least one signal processor, and wherein the at least one signal processor is physically separate from the at least one memory device and is configured to process signals received from the at least one memory device; and
  a gas delivery control system configured to:
    receive the electrical signals from the plurality of electronic devices embedded within the sidewall of the patient interface device via the connection interface; and
    control a function of the gas delivery apparatus based at least on the electrical signals received from the one or more electronic devices.

16. A system according to claim 15, wherein:
  the connection interface is configured to provide the electrical interface for receiving electrical signals communicated by one or more sensors at least partially embedded within the sidewall of the patient interface device, wherein the one or more sensors are physically separate from the at least one signal processor; and
  the gas delivery control system is configured to control the gas delivery apparatus based at least on the electrical signals received from the one or more sensors.

17. A system according to claim 15, wherein:
  the connection interface is configured to provide an electrical interface configured to receive electrical signals communicated by the at least one signal processor embedded within the sidewall of the patient interface device; and
  the gas delivery control system is configured to control the gas delivery apparatus based at least on the electrical signals received from the at least one signal processor.

18. A medical device, comprising:
  a gas delivery apparatus configured to deliver gas toward a patient;
  a patient interface device communicatively coupled to the gas delivery apparatus, the patient interface device having a connection end configured to couple to the gas delivery apparatus and a patient end configured to be disposed proximate the patient;
  a plurality of electronic devices embedded within a sidewall of the patient interface device proximate the patient end and configured to produce electrical signals, wherein the plurality of electronic devices comprise at least one memory device and at least one signal processor, and wherein the at least one signal processor is physically separate from the at least one memory device and is configured to process signals received from the at least one memory device; and
  an electrical circuit configured to communicate the electrical signals from the plurality of electronic devices to the gas delivery apparatus, the electrical circuit having a plurality of contacts proximate the connection end of the patient interface device and having a plurality of electrical conductors at least partially embedded within the sidewall of the patient interface device to couple the plurality of contacts to the plurality of electronic devices.

19. A medical device according to claim 18, comprising one or more sensors at least partially embedded within the sidewall of the patient interface device, wherein the one or more sensors are physically separate from the at least one signal processor.

20. A medical device according to claim 18, further comprising a gas delivery control system configured to control a function of the gas delivery apparatus based at least on electrical signals received from the one or more electronic devices via the electrical circuit.

21. A method of communicating data in a breathing assistance system, comprising:
  operating a system comprising:
    a patient interface device configured to be used in a breathing assistance system, the patient interface device comprising:
      a connection end configured to receive gas communicated by a gas delivery apparatus, the connection end having a plurality of contacts; and
      a patient end configured to be inserted into one or more breathing passageways of a patient;
    a plurality of electronic devices embedded within a sidewall of the patient interface device proximate the patient end, the plurality of electronic devices configured to generate electrical signals and comprising at least one memory device and at least one signal processor, and wherein the at least one signal processor is physically separate from the at least one memory device and is configured to process signals received from the at least one memory device; and one or more electrical conductors at least partially embedded within the sidewall of the patient interface device, the one or more electrical conductors coupling the plurality of electronic devices to the plurality of contacts to facilitate communication of the electrical signals from the plurality of electronic devices to the gas delivery apparatus when the patient interface device is communicatively coupled to the gas delivery apparatus; and communicating the electrical signals between the plurality of electronic devices and the gas delivery apparatus via the one or more electrical conductors.

* * * * *